United States Patent [19]

King et al.

[11] Patent Number: 5,089,532
[45] Date of Patent: Feb. 18, 1992

[54] CATALYST, METHOD OF PRODUCING AND USING SAME FOR PRODUCTION OF METHANOL AND HIGHER ALCOHOLS

[75] Inventors: Terry S. King, Ames, Iowa; Gordon R. Sheffer, South Charleston, W. Va.

[73] Assignee: Iowa State University Research Foundation, Inc., Ames, Iowa

[21] Appl. No.: 329,860

[22] Filed: Mar. 28, 1989

[51] Int. Cl.$^5$ ............................................. C07C 27/06
[52] U.S. Cl. ..................................................... 518/713
[58] Field of Search ........................................ 518/713

[56] References Cited

U.S. PATENT DOCUMENTS

| | | | |
|---|---|---|---|
| 3,326,956 | 6/1967 | Davis et al. | 518/713 |
| 3,689,575 | 9/1972 | Tarhan | 260/632 |
| 4,031,123 | 6/1977 | Espino et al. | 260/449.5 |
| 4,112,110 | 10/1978 | Sugier et al. | 260/449.5 |
| 4,144,401 | 3/1979 | Wall | 568/840 |
| 4,291,126 | 9/1981 | Sugier et al. | 518/713 |
| 4,342,838 | 8/1982 | Pruett et al. | 518/713 |
| 4,423,265 | 12/1983 | Chu et al. | 585/322 |
| 4,477,594 | 10/1984 | Greene et al. | 518/700 |
| 4,559,207 | 12/1985 | Hiller et al. | 555/860 |
| 4,576,968 | 3/1986 | Nay et al. | 518/713 |
| 4,598,061 | 7/1986 | Schneider et al. | 502/303 |

OTHER PUBLICATIONS

Natta, Catalysis, vol. III, Ed. P. Emmett, Reinhold Publishing, New York, 1955, p. 373.

Vedage et al., Symposium on Role of Solid State Chemistry in Catalysis, Div. of Petroleum Chemistry, A.C.S. Washington, D.C. Meeting 8-28 to 9-2, 1983, pp. 1261-1271.

Hu et al. C.A. 108: 16907n, Shiyou Xuebao, Shiyou, Jiayong 1986 2(4) 87-93.

Eguchi, Fuel Economist, vol. 11, 1936, 417-419.

Primary Examiner—Howard T. Mars
Attorney, Agent, or Firm—Zarley, McKee, Thomte, Voorhees & Sease

[57] ABSTRACT

The invention relates to a catalyst and method of making and using same for primary alcohols from synthesis gas. It employs a Group IA alkali metal promoter with copper for a high selectivity and productivity in producing methanol and higher alcohols. Under higher temperatures, and lower hydrogen to carbon monoxide ratios, the catalyst is selective for higher linear alcohols.

4 Claims, 1 Drawing Sheet

CATALYST, METHOD OF PRODUCING AND USING SAME FOR PRODUCTION OF METHANOL AND HIGHER ALCOHOLS

BACKGROUND OF THE INVENTION

This invention relates to a catalyst composition for use in the production of methanol, and methanol and higher alcohol mixtures from synthesis gas.

Methanol has in the past been produced from exposure of synthesis gas to a alkali-free, copper-zinc oxide-based catalyst. In a similar manner, higher alcohols, primarily isobutanol, can be produced by an alkali promoted copper-zinc oxide catalyst. In addition, linear alcohols can be produced by copper-based catalysts composed of a mixture of several metals including ruthenium, cobalt, chromium and thorium. Synthesis gas is mainly a combination of $H_2$ and CO.

Interest in these processes has increased with the advent of alcohol-gasoline fuel mixtures. Further, it has been found improved results in gasoline mixtures occur within a mix of methanol and higher aliphatic alcohols, or higher aliphatic alcohols alone.

A disclosure demonstrating a process to produce methanol is found in U.S. Pat. No. 3,326,956 by Davies and Snowden. Synthesis gas is passed over a catalyst containing copper, zinc and chromium oxides. Also, U.S. Pat. No. 4,565,802 by Suhoenthal and Slaugh gives the elements copper, zinc and aluminum as the catalyst. Both are incorporated herein by reference and teach that care must be taken to eliminate electrolytes such as alkali metal in order to produce highly active and selective catalysts.

The productivity normalized to surface areas for these types of catalysts are typically 2 to $5 \times 10^{-5}$ by methanol per hour per $m^2$.

A disclosure demonstrating a process to produce a mixture of methanol and higher alcohols is found in U.S. Pat. No. 4,122,110 by Sugier, et al. Synthesis gas is passed over a catalyst having the four elements copper, cobalt, an alkali metal and a metal selected from chromium, iron, vanadium, and manganese to produce methanol and higher alcohols. Production is reported to be higher than 100 Kg of $C_2+$ or higher alcohols per cubic meter of catalyst with selectivity to alcohols 95% or higher, selectivity to linear saturated alcohols of $C_2$ or more often higher than 70% by weight using the preferred method. The production rate to methanol plus higher alcohols is about $1 \times 10^{-5}$ Kg per $m^2$ per hour.

A catalyst comprising cobalt, and one or more of copper, silver, gallium, zirconium, zinc and thorium; one or more of palladium, platinum, and nickel; and one or more alkali metals was also recently disclosed by Nay et al. in U.S. Pat. No. 4,576,968. This catalyst is used with synthesis gas to obtain saturated straight-chain primary alcohols such as methanol, ethanol, propanol and butanol.

These attempts to improve higher alcohol production all require that the copper and an alkali metal be combined with a number of other elements. This expensive catalyst mixture is quite complex and requires great care in preparation to ensure the appropriate form is produced.

The catalysts demonstrated in the production of methanol, on the other hand, do not use alkali metals but require copper be combined with at least one other element.

This invention is premised on the discovery that copper may be used alone as the catalyst, employing only a small amount of an alkali promoter selected from Group IA elements.

Methanol may be produced exclusively or a methanol-higher alcohol mixture may be produced depending on the choice of alkali metal and reaction conditions. For example, a copper./potassium catalyst can produce methanol at a rate (based upon surface area) of 2 to 5 times greater than obtained with a copper-zinc oxide catalyst impregnated with cesium. It is demonstrated that the promotional effect increases monotonically from lithium to cesium, with the largest jump between sodium and potassium. Copper promoted with lithium can produce methanol and linear, higher alcohols yielding 30 percent by weight ethanol and higher alcohols. The surprising advantages occur from using only copper combined with the Group IA element, making the catalyst easier to produce and providing for a variety of ways in which to make the catalyst.

Accordingly, it is an object of the invention to provide a catalyst composition and method of producing and using the same suitable for use in producing methanol or methanol and higher alcohols, using copper along with a Group IA element promoter.

Another object is to provide a catalyst method of producing and using the same which is highly selective for $C_2 +$ alcohols.

Another object of the invention is to provide a catalyst and method of producing and using the same which is highly selective for methanol.

A further object is to provide a catalyst which is easy to produce.

BRIEF SUMMARY OF THE INVENTION

This invention relates to a catalyst and method of using and producing same which is useful in producing methanol or a mixture of methanol and primary linear alcohols wherein copper is combined with a small amount of an alkali promoter selected from the group consisting of Group IA elements (e.g., Li, Na, K, Rb, Cs). This catalyst is highly selective for methanol when using typical methanol-synthesis conditions (high hydrogen to carbon monoxide feed gas ratios), and is highly selective for higher alcohols when lithium is used as the promoter and lower hydrogen to carbon monoxide ratios.

DETAILED DESCRIPTION OF THE DRAWINGS

DETAILED DESCRIPTION OF THE INVENTION

Figure 1:
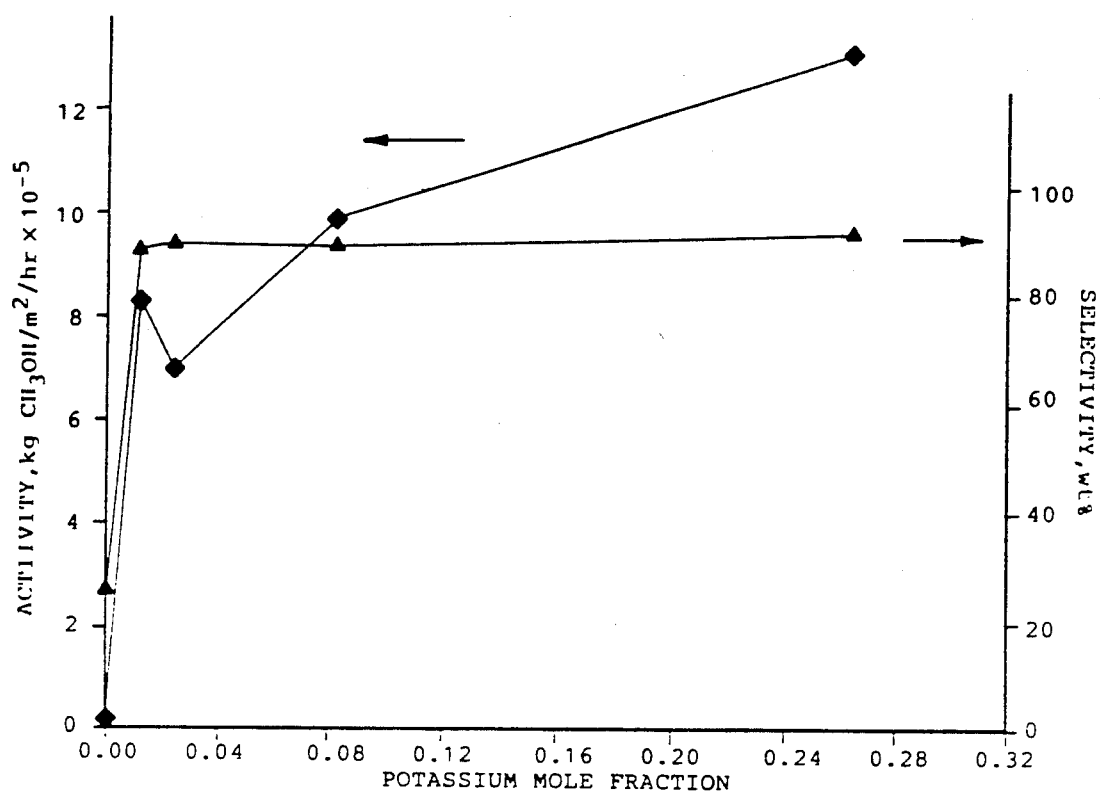
FIG. 1 is a graph depicting resulting catalytic activity and selectivity for carbon monoxide hydrogenation as a factor of potassium content, employing this invention.

Under reaction conditions, copper exists as a mixture of $Cu^+$ and $Cu^\circ$ species. Metallic copper by itself is not active for hydrogenation of carbon monoxide. To date, use of copper in a catalyst system for synthesis of methanol or higher alcohols has always included other metals in combination with the copper. The ability of Group IA elements to promote synthesis of the primary alcohols for unsupported copper-alkali catalysts has not been previously investigated or shown. Indeed, for methanol synthesis catalysts, prior work has called for the exclusion of alkali metals.

Overall, synthesis gas or $H_2/CO$ in a ratio of 0.1:1 to 10:1 is passed over the catalyst at a temperature of 450° K. to 650° K. at 10 atmospheres to 400 atmospheres. The catalyst is copper which can take any of its various forms, including its cation. The amount of copper used is a catalytically effective amount, from 0.1 to 99.9 percent by weight. The smallest effective amount would be ordinarily used for economic reasons. It is combined with Group IA promoter so that the alkali metal makes up 0.01 weight % to 30 weight percent of the catalyst, with copper making up the remaining amount of the catalystic material. The copper and alkali promoter may be in a finely divided state on a typical inert catalyst support (e.g. silica) of the type widely used in catalyst preparation. The reaction time can be referred to as gas hourly space velocity and would include a range of 100 to 100,000 inverse hours, with a range of 1,000 to 20,000 inverse hours preferred.

Methanol was selectively produced on all catalysts at 523° K., 5 MPa (50.5 atmospheres) and with a feed gas of molar composition $H_2/CO=2:1$. The methanol synthesis rate increased by an order of magnitude from lithium to cesium with a majority of increase occurring from sodium to potassium. On the basis of apparent activation energy measurements, x-ray photo-electron spectroscopy, and scanning electromicroscopy results, activity differences were attributed to differences in the concentration of cuprous species at the surface and not electronic effects. The initiation of catalytic activity correlated with stabilization of the cuprous species. In particular, the results with the potassium promoter show that this catalyst is promoted by potassium by stabilizing the cuprous species. Under conditions more favorable for higher alcohol synthesis, 573° K. and $H_2/CO=1:1$, good selectivity for the higher alcohols was enhanced, most notably for the lithium promoted catalysts.

The invention is not limited to unsupported copper, but may employ copper supported on a typical catalyst support, such as silica, alumina or magnesium oxide.

Catalysts are prepared by any of the known methods, including that which is outlined by Courty, P., Durand, D., Freund, E., and Sugier, A., *J. Mol. Catal.* 17, 241 (1982). Typically, citric acid is added to an aqueous solution of the copper salt and a promoter salt, with the resulting solution evaporated, dried and then calcinated. Any salt form may be used, with a water soluble copper salt preferred and cupric nitrate most preferred. An alternate procedure for producing the catalyst is to directly impregnate a copper catalyst with an aqueous solution of the Group IA salts. Another alternate method is to directly impregnate a catalyst support with copper and alkali metal salt solutions. The amount of Group IA promoter may range from 0.01 wt. % to 30 wt. %, with the preferred range involving 0.1 wt. % to 10 wt. % of the catalyst and copper making up the remaining amounts. When a support is used, the range preferred would be 0.1 to 20 wt. % Group IA promoter in the catalyst and 1 to 20 wt. % copper. With the increased amounts of the promoter, activity is seen to increase while selectivity stays about the same. Addition of only 0.012 mol % of potassium to unsupported copper caused the methanol synthesis rate to increase to $8.3 \times 10^{-5}$ kg/m$^2$/hr.

The catalysts were tested and placed within a reaction vessel. Any acceptable reactor type would be workable, and in this case was a stainless steel tube fixed-bed reactor. The reaction studies employed an $H_2/CO/Ar$ synthesis gas. Argon served as an internal standard for calculation of activity.

In order to produce methanol, the temperature range falls within 450° K. to 650° K., with the range of 500° K. to 570° K. preferred. In order to produce the higher alcohols, the temperature range is the same, with 550° K. to 600° K. preferred. The pressure employed for these reactions was generally 5MaP (mega pascals), or 50 atmospheres. For methanol synthesis, it can range from a low of 10 atmospheres to a high of about 200 atmospheres, with 20 to 100 atmospheres preferred. Higher alcohol synthesis would include a range of 40 atmospheres to 400 atmospheres with 40 to 200 atmospheres preferred. The $H_2/CO$ ratio can range from 0.1:1 to 10:1, and a ratio of 0.5:1 to 5:1 is the best, and a ratio of 0.5:1 to 1:1 the most preferred for producing higher alcohols and 2:1 to 5:1 for methanol.

The following examples are given to illustrate the scope and spirit of the invention. Since they are illustrative, the invention should not be considered as being limited to them.

EXAMPLE 1

Catalysts were prepared by methods similar to those outlined by Courty, supra. Briefly, citric acid was added to aqueous solutions of cupric nitrate and potassium nitrate to yield one gram equivalent of acid per gram equivalent of copper and potassium. The resulting solution was evaporated under vacuum at room temperature to form a thick slurry. The slurry was dried overnight at 353° K. The solid obtained was then calcined at 623° K. in air for 4 hours. It was observed that at approximately 473° K. the catalyst precursor rapidly decomposed with the evolution of large amounts of heat and gas. The potassium-to-copper molar ratio of the calcined catalysts were verified by flame emission and atomic absorption spectroscopies.

For purposes of comparison, two alternate preparation procedures were used. The first used the same technique as outlined above except that cupric acetate was substituted for cupric nitrate. The second procedure was a direct impregnation of reagent grade cupric oxide with an aqueous solution of potassium carbonate.

All catalysts were tested in a single-pass, fixed-bed, flow microreactor system outlined. The unit was designed for operation up to 623° K. and 15 MPa. Feed gases were $H_2$ (>99.995%), Ar (>99.995%), and CO (>99.3%), which were further purified with molecular sieve size 4 angstroms. Gases were metered by use of Brooks mass flow controllers.

The reaction vessel consisted of a 0.25 m, type 304 stainless steel tube of 0.0092 in internal diameter. The amount of reaction occurring on the reactor and tubing walls in the system was found to be negligible by blank runs where the reactor was filled with powdered quartz. An air-fluidized aluminum-oxide bath regulated by a time-proportional controller was used to maintain reactor temperature. The internal reactor temperature was measured by a subminiature thermocouple moved within a stainless steel protection sheath positioned axially in the reactor.

To maintain elevated reactor pressure, an air-actuated pressure control valve was placed downstream from the reactor. To avoid condensable products, the controller for the valve sensed the inlet reactor pressure. To minimize reactor pressure drop and avoid internal heat and mass transport limitations, the reactor was loaded with catalyst particles of 0.13 to 0.25 mm diameter (60/100 mesh).

On-line product analysis was performed by gas chromatography after 15 minutes on stream and then at one hour intervals. Samples were collected at elevated temperature and atmospheric pressure by using two gas sampling valves with 0.5 ml sample loops. All post-reactor lines and valves were heated to reaction temperature in order to avoid product condensaton. Organic products were separated with a 0.00025 m ID, 30 m Supelco SPB-1 capillary column operated with a split ratio of approximately 80:1. Ar, CO, and $CO_2$ were separated on a Supelco S-2 carbosieve column. $H_2$ and $H_2O$ concentrations were not determined. The various products were detected by use of a flame ionization detector and a thermal conductivity cell. Both columns were located in a single oven, which was ramped from 263° K. to 553° K. at 10 K/min for maximum product separation. Data were acquired and analyzed with a Spectra-Physics 4000 lab station.

All reaction studies employed a $H_2/CO/Ar$ synthesis gas of molar composition 2/1/0.5 at a gas hourly space velocity of 4000 $hr^{-1}$. Argon served as an internal standard for calculation of activity. Temperature and total pressure were maintained at 548° K. and 5 MPa, respectively. Before synthesis gas exposure, the calcined catalysts were reduced in situ with a mixture of 10% $H_2$ in argon mixture at atmospheric pressure and 548° K. With this pretreatment procedure unpromoted cupric oxide was found by thermal gravimetric analysis to reduce completely to copper metal within 15 minutes. A small temperature gradient (5°-10° K.) passed quickly through the reactor during pretreatment. No temperature gradient was noted during synthesis gas reaction.

Catalytic activity and selectivity for carbon monoxide hydrogenation as a function of potassium content, resulting from the procedures outlined in Example 1 are plotted in FIG. 1. The X-axis on the left shows catalytic activity in methanol produced per meter square per hour x $10^{-5}$, as a function of the amount of potassium, reflected in the Y axis. Selectivity to carbon monoxide hydrogenation is shown in the X axis on the right, as a function of potassium content.

The results reported are the values found after the catalyst had been on-stream for 10 hours. Methanol was produced immediately upon synthesis gas exposure, and the rates varied little over the first ten hours. Activities were normalized with respect to the surface area of used catalyst. The selectivity to methanol was high (93 to 98 Wt %) with methane as the only by-product. Unpromoted copper was found to be inactive. As reported, addition of 0.012 mol % potassium to copper caused the methanol synthesis rate to increase to $8.3 \times 10^{-5} kg/m^2/hr$.

The potassium carbonate impregnated cupric oxide catalyst had activity comparable to cupric nitrate derived catalysts. The cupric nitrate derived catalyst demonstrated a methanol activity of 7 $kg/m^2/hr \times 10^{-5}$, while the potassium carbonate impregnation of cupric oxide yielded a methanol activity rate of 4.8 $kg/m^2/hr \times 10^{-5}$. Hence, the promoting effect of potassium may be imparted through simple impregnation as well as the more involved citrate complex preparation previously outlined.

It was noted that potassium dispersion in the unsupported copper system is desired, in that an alternative preparation using cupric acetate in place of cupric nitrate demonstrated through x-ray photoelectron spectroscopy and scanning electron microscopy data that the concentration of potassium into needle clusters on the surface resulted in a decrease in the amount of $Cu^+$ species at the surface in a subsequent decreasing catalytic activity. The poor potassium dispersion in this catalyst probably resulted from poor water solubility of cupric acetate. The ability to promote methanol synthesis on cupric oxide by potassium carbonate impregnation demonstrates that copper on a high surface area support would also be promoted by potassium impregnation.

The catalytic behavior reagent grade potassium carbonate shows that it is inactive for carbon monoxide hydrogenation, as is the unpromoted copper catalyst. Hence, there is a truly synergistic effect involved in the synthesis of methanol on unsupported potassium-copper catalysts.

EXAMPLE 2

Catalyst preparation was accomplished as set out above. Copper and alkali concentrations were verified by atomic absorption and flame emission spectroscopies of the calcined catalysts.

Catalysts were evaluated in a single-pass, fixed-bed microreactor system detained above. All catalysts were reduced in situ before synthesis gas exposure by use of a 10% $H_2$ in argon gas mixture at 523° K. and atmospheric pressure. A small temperature rise (10° to 15° K.) was noted initially upon hydrogen exposure.

The methanol synthesis activity of the copper alkali catalyst, as set forth in Example 2, is summarized in Table 1 below.

TABLE 1

| | Initial and Steady-state Methanol synthesis rates[a] | | | |
|---|---|---|---|---|
| | Activity (kg/g cat/hr) $\times 10 + 5$ | | Activity (kg/m²/hr) $\times 10^{+5}$ | |
| Alkali | Initial | Steady State | Initial | Steady State |
| None | 0 | <0.2 | 0 | <0.2 |
| Li | 1.7 | 1.0 | 1.0 | 1.0 |
| Na | 1.6 | 1.4 | 2.0 | 2.1 |
| K | 9.6 | 5.1 | 12 | 15 |
| Rb | 4.9 | 3.1 | 14 | 18 |
| Cs | 2.6 | 1.4 | 18 | 14 |

[a]T = 523 K, P = 5 PMa, $H_2/CO$ = 2, GHSV = 4000 $hr^{-1}$.

As previously noted, the unpromoted copper catalyst is inactive. For promoted catalysts, the selectivity to methanol was greater than 98 Wt. % in all cases except for lithium where the selectivity was 90 mol %. As can be seen, the methanol synthesis rate on unsupported copper-alkali catalysts was found to increase by an order of magnitude progressively from lithium to cesium. Interestingly, most of this increase occurs from sodium to potassium, with the activity of lithium and sodium promoted catalysts being comparable and that of potassium, rubidium, and cesium promoted catalysts being comparable. A steady-state methanol synthesis rate for potassium, rubidium, and cesium promoted copper catalyst was approximately $15 \times 10^{-5} kg/m^2/hr$, which is a factor 5 greater than the $3 \times 10^{-5} kg/m^2/hr$ value reported for a cesium promoted, copper-zinc oxide catalyst at 523° K., 7.5 MPa with a synthesis gas of molar composition $H_2/CO=2.3$. (Nunan, J. G., Klier, K., Young, C. W. Himmelfarb, P. B., Herman, R. G., J. Chem. Soc. Commun. 1986, 193.)

EXAMPLE 3

Conditions were the same as set forth in Example 2, except that the reaction temperature was raised to 573° K. and the $H_2/CO$ molar ratio was lowered to 1:1.

For the Na, K, Rb, and Cs promoted catalysts the selectivity to methanol was still quite good even at less than optimum conditions. Surprisingly, the lithium promoted catalyst exhibited good selectivity to methanol and higher alcohols at these same conditions.

TABLE 2

Activity and selectivity of copper-alkali catalysts under higher alcohol synthesis conditions.[a]

| | | Selectivity (mol %) | | | | |
|---|---|---|---|---|---|---|
| | Activity × $10^{-3}$ | Hydrocarbons | | Alcohols | | |
| Alkali | (mol CO/m²/hr) | $C_1$ | $C_2+$ | $C_1$ | $C_2$ | $C_3+$ |
| Li | 0.6 | 31.1 | 18.7 | 40.8 | 6.9 | 2.5 |
| Na | 0.3 | 10.6 | 2.4 | 87.0 | — | — |
| K | 2.3 | 1.4 | — | 98.0 | 0.6 | — |
| Rb | 3.5 | 1.4 | 0.3 | 98.2 | 0.1 | — |
| Cs | 9.3 | 2.2 | 0.7 | 96.8 | 0.4 | — |

[a]T = 573 K, P = 5 MPa, $H_2/CO$ = 1, GHSV = 4000 hr$^{-1}$.

Figure 2:
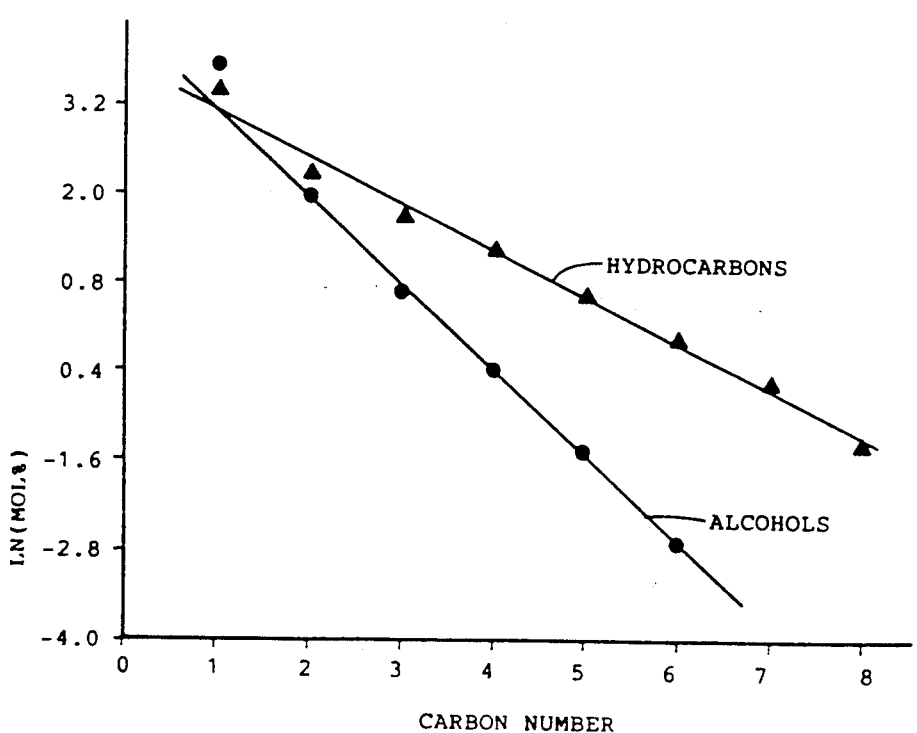
FIG. 2 is a graph indicating the distribution of alcohols and hydrocarbons produced employing this invention.

Unlike alkali promoted copper-zinc oxide catalyst where significant branching is observed, the higher alcohols formed were linear. Moreover, the distribution of both alcohols and hydrocarbons was consistent with Flory theory (see FIG. 2). P.J. Flory, J. American Chemical Society 58, 1877 (1936). The chain growth probability factors were substantially different with values of 0.30 for alcohols, and 0.53 for hydrocarbons. When the mole fractions of both functionalities were combined, the chain growth probability factor of 0.37 was obtained.

Although the invention has been described with a certain amount of particularity, it will be realized by those skilled in the art that certain changes and modifications can be made without departing from the spirit and scope of the claimed invention.

Thus, it can be seen from the foregoing that the invention accomplishes at least all of its objectives.

What is claimed is:

1. In a process for manufacturing primary linear alcohols by contacting a gaseous mixture comprising carbon monoxide and hydrogen with a catalyst, the improvement comprising:
   conducting the process in the presence of a catalyst consisting of a catalytically effective amount of copper and a lithium promoter;
   said process being conducted at a temperature of from about 550° K. to about 600° K. at a ratio of carbon monoxide to hydrogen of from about 0.5:1 to 1:1 and at a pressure of from 40 atmospheres to 400 atmospheres thus making the process selective for manufacturing a mixture of methanol and higher alcohols.

2. The process of claim 1 wherein said catalyst is from about 0.01 wt. % to about 30 wt. % of a lithium promotor.

3. The process of claim 1 wherein said copper is supported.

4. The process of claim 1 wherein said copper is unsupported.

* * * * *